United States Patent [19]

Uphues et al.

[11] Patent Number: 4,921,990
[45] Date of Patent: May 1, 1990

[54] DIRECT ESTERIFICATION OF O-PHOSPHORIC ACID

[75] Inventors: Guenter Uphues, Monheim; Uwe Ploog, Haan, both of Fed. Rep. of Germany

[73] Assignee: Henkel Kommanditgesellschaft auf Aktien, Düsseldorf, Fed. Rep. of Germany

[21] Appl. No.: 393,082

[22] Filed: Aug. 8, 1989

Related U.S. Application Data

[63] Continuation of Ser. No. 133,600, Dec. 16, 1987, abandoned.

[30] Foreign Application Priority Data

Dec. 20, 1986 [DE] Fed. Rep. of Germany ....... 3643763

[51] Int. Cl.$^5$ .............................................. C07F 9/141
[52] U.S. Cl. ..................................... 558/104; 558/105
[58] Field of Search ................................ 558/104, 105

[56] References Cited

U.S. PATENT DOCUMENTS

| | | | |
|---|---|---|---|
| 3,439,067 | 4/1969 | Austin et al. | 558/104 |
| 3,641,219 | 2/1972 | Stockburger | 558/105 |
| 4,350,645 | 9/1982 | Kurosaki et al. | 260/978 |

FOREIGN PATENT DOCUMENTS 1100589  5/1986  Japan .................... 558/104

OTHER PUBLICATIONS

Holleman, Lehurbuch der Anorganischen Chemie, 1976, p. 453.
Houben-Weyl, Derivative der Orthophosphorsäure, p. 143.

Primary Examiner—Jacqueline V. Howard
Attorney, Agent, or Firm—Ernest G. Szoke; Wayne C. Jaeschke; Henry E. Millson, Jr.

[57] ABSTRACT

A process for the direct esterification of o-phosphoric acid with aliphatic fatty alcohols and/or adducts thereof with alkylene oxides and alkylphenol alkoxylates, in the presence of a substoichiometric quantity of a basic, inorganic or organic compound and a water-entraining agent.

12 Claims, No Drawings

DIRECT ESTERIFICATION OF O-PHOSPHORIC ACID

This application is a continuation of application Ser. No. 33,600 filed Dec. 16, 1987, now abandoned.

BACKGROUND OF THE INVENTION

1. Field of the Invention:

This invention relates to the direct esterification of o-phosphoric acid with fatty alcohols, alkoxylated fatty alcohols and alkylphenol alkoxylates in the presence of a water entraining agent and at least one inorganic or organic base.

2. Statement of Related Art:

According to D. Sasse in "Houben-Weyl", Vol. 12, "Organische Phosphorverbindungen (Organic Phosphorus Compounds)", Part 2, page 143, the esterification of o-phosphoric acid with hydroxy compounds involves the formation of di- or polyphosphoric acids which then undergo alcoholic cleavage.

From Hollemann-Wiberg, "Lehrbuch der anorganischen Chemie", 83rd to 90th Edition, page 453, 1976, it is known for example that, at temperatures above 200° C, o-phosphoric acid is converted with intermolecular elimination of water into diphosphoric acid which, in turn, changes via even higher polyphosphoric acids into metapolyphosphoric acid at temperatures above 300° C with further elimination of water.

Since the primary reaction mainly takes place at temperatures of at least 170° C., olefin is split off from the ester formed in a secondary reaction. Due to the relatively high vapor pressure of the olefins, the reaction temperature falls during the esterification and no more ester is formed.

The olefin formation is presumably the reason why no literature can be found on the direct esterification of fatty alcohols with o-phosphoric acid alone without the further use of phosphorus-containing substances.

U.S. Pat. No. 4,350,645 describes an esterification process using o-phosphoric acid. However, the o-phosphoric acid is not used on its own, but is used together with phosphorus pentoxide.

According to K. Sasse (loc. cit.), the reaction of a fatty alcohol with o-phosphoric acid proceeds up to an equilibrium in which the concentration of the ester formed is substantially proportional to the square of the concentration of the phosphoric acid. The establishment of the equilibrium is relatively quick in the case of lower alcohols, but rapidly decreases with increasing chain length of the aliphatic radical.

DESCRIPTION OF THE INVENTION

Other than in the operating examples, or where otherwise indicated, all numbers expressing quantities of ingredients or reaction conditions used herein are to be understood as modified in all instances by the term "about".

An object of the present invention is to provide a process for the direct esterification of o-phosphoric acid with alcohols in which there is no need for the additional use of phosphorus-containing compounds.

Another object of the present invention is, where possible, to remove the unreacted alcohol from the reaction mixture by distillation without olefin formation.

More specifically, the present invention relates to a process for the production of phosphoric acid alkyl ester mixtures wherein from 1 to 5 mole equivalents of a saturated or unsaturated $C_6$-$C_{18}$ fatty alcohol and preferably a linear or branched, $C_8$-$C_{18}$ fatty alcohol, or an adduct thereof containing from 1 to 20, and preferably from 1 to 12, moles of ethylene oxide and/or propylene oxide, and/or an adduct of from 1 to 20 moles of ethylene oxide and/or propylene oxide with alkylphenols containing from 8 to 15 carbon atoms in the alkyl substituents, for example adducts of from 1 to 20 moles of ethylene oxide and/or propylene oxide with nonylphenol, are directly esterified with 1 mole equivalent of o-phosphoric acid in the presence of from 0.05 to 0.2 mole equivalent, based on the quantity of phosphorus atoms present in the reaction mixture, of a basic (i.e. alkaline) inorganic or organic compound or a mixture of such compounds and a water-entraining agent with removal of the water of reaction from the reaction system.

In the context of the invention, fatty alcohols include, inter alia, hexyl alcohol, 2-ethylhexyl alcohol, heptyl alcohol, octyl alcohol, nonyl alcohol, isononyl alcohol, decyl alcohol, isodecyl alcohol, undecyl alcohol, dodecyl alcohol, tridecyl alcohol, isotridecyl alcohol, tetradecyl alcohol, pentadecyl alcohol, hexadecyl alcohol, heptadecyl alcohol, octadecyl alcohol, oleyl alcohol, elaidyl alcohol, and isostearyl alcohol.

Amines and alkali metal hydroxides are preferably used as the basic inorganic or organic compound. It is particularly preferred to use amines without any additional functional groups and having molecular weights in the range of from 129 to 297, for example dimethyl cocosamine, or potassium or sodium hydroxide.

According to the invention, suitable water-entraining agents include, inter alia, $C_1$-$C_4$ alkyl benzenes, e.g. toluene and xylene.

Another feature of the present invention is that the esterification is carried out at a temperature of at least 160° C., usually in the range of from 130° to 250° C., preferably 160°-200° C.

Another feature of the present invention is that unreacted fatty alcohols can be directly removed from the reaction mixture by vacuum distillation.

Phosphoric acid esters prepared in accordance with the invention may be converted by known methods into their alkali metal salts, ammonium salts and alkanolamine salts, e.g. $C_1$-$C_4$ alkanolamine salts. Salts of this type are widely used as cleaning preparations, emulsifiers, antistatic agents and rustproofing agents or the like. One advantage of the process of the invention is that the condensation reaction is distinctly accelerated. In addition, relatively high yields of di- and trialkyl ester can be obtained which cannot be obtained using phosphorus pentoxide. In one embodiment of the invention, unreacted alcohol may be directly removed from the reaction mixture by distillation before neutralization without olefin formation. The products obtained are very light in color.

The invention will be illustrated but not limited by the following examples.

EXAMPLES

In each of the following examples of the invention, the terms "monoalkyl ester", "dialkyl ester", and "trialkyl ester" refer to esters of phosphoric acid wherein the alkyl group or groups correspond to the alkyl groups in the alcohols employed in the reaction.

EXAMPLE 1

198 g (1.5 moles) n-octanol (OH number 425), 23.7 g (0.1 mole) dimethyl cocosamine, 0.3 g hypophosphorous acid (50%) and 40 ml toluene were introduced into a stirring apparatus equipped with a water separator, reflux condenser and thermometer. 115.2 g (1.0 mole) phosphoric acid (85%) were added with stirring. The mixture was then heated until it boiled vigorously under reflux. During the separation of water which began at 130° C., the temperature rose to 182° C. After 6 h, a total of 42.6 g of water had been separated off and the reaction was terminated.

The toluene was removed by distillation in a vacuum of 20 mbar and at a final temperature of 110° C. 282.6 g of a colorless oily liquid were obtained as residue.

The composition of the residue was analyzed by multistage potentiometric titration and determination of the phosphorus and amine content:
- 34.0% monoalkyl ester
- 42.2% dialkyl ester
- 11.8% trialkyl ester
- 3.4% o-phosphoric acid
- 0.0% n-octanol
- 8.4% dimethyl cocosamine Other additions according to the invention were carried out under the same conditions.

| Example No. | Addition | Yield (g) | Composition (%) | | | | | |
|---|---|---|---|---|---|---|---|---|
| | | | mono-ester | di-ester | tri-ester | o-phos-phoric acid | octa-nol | addi-tion |
| 2 | potassium hydroxide | 261.6 | 30.2 | 60.0 | 0.0 | 0.8 | 7.1 | 1.9 |
| 3 | cocosamine | 265.2 | 21.0 | 63.2 | 0.9 | 5.0 | 3.2 | 6.7 |
| 4 | tributyl amine | 275.5 | 37.9 | 45.1 | 3.4 | 2.2 | 5.0 | 6.4 |
| 5 | N-lauryl diamino-propane | 266.5 | 31.1 | 40.8 | 13.1 | 5.2 | 5.3 | 4.5 |

EXAMPLE 6

195 g (1.5 moles) 2-ethylhexanol, 23.7 g (0.1 mole) dimethyl cocosamine, 0.3 g hypophosphorous acid (50%) and 115.2 g (1.0 mole) phosphoric acid (85%) were reacted in the presence of 40 ml toluene in an apparatus equipped as described in Example 1.

The maximum temperature was 161° C. and 43.6 g water were separated off. Removal of the toluene left 270.1 g of a colorless oily residue which had the following composition:
- 45.3% monoalkyl ester
- 26.4% dialkyl ester
- 3.8% trialkyl ester
- 6.2% o-phosphoric acid
- 10.1% 2-ethyhexanol
- 8.2% dimethyl cocosamine

EXAMPLE 7

390 g (1.5 moles) tallow alcohol (OH number 315.8; iodine number 1), 23.7 g (0.1 mole) dimethyl cocosamine, 0.5 g hypophosphorous acid (50%) and 115.2 g (1.0 mole) phosphoric acid (85%) were reacted in the presence of 75 ml toluene in an apparatus equipped as described in Example 1. The quantity of water separated off with a maximum temperature of 189° C. was 45.3 g. Removal of the toluene left 487 g of a residue which solidified on cooling (iodine number 1.6). The following composition was calculated from the total analysis:
- 20.9% monoalkyl ester
- 42.1% dialkyl ester
- 18.1% trialkyl ester
- 4.9% o-phosphoric acid
- 7.5% tallow alcohol
- 1.6% tallow olefin
- 4.9% dimethyl cocosamine

EXAMPLE 8

282 g (1.5 moles) n-dodecanol (OH number 298), 23.7 g (0.1 mole) dimethyl cocosamine, 0.3 g hypophosphorous acid (50%) and 115.2 g (1.0 mole) o-phosphoric acid were reacted in the presence of 40 ml toluene in an apparatus of the type described in Example 1. The quantity of water separated off was 45.0 g with a maximum temperature of 198° C. Removal of the toluene left 375 g of a residue which solidified on cooling (iodine number 2.2). The composition was as follows:
- 28.0% monoalkyl ester
- 43.6% dialkyl ester
- 10.1% trialkyl ester
- 4.6% o-phosphoric acid
- 7.3% n-dodecanol
- 6.4% dimethyl cocosamine

EXAMPLE 9

273 g (0.75 mole) of a mixture of dodecyl and tetradecyl alcohol reacted with 4 moles ethylene oxide, 11.8 g (0.05 mole) dimethyl cocosamine, 0.3 g hypophosphorous acid (50%), 57.6 g (0.5 mole) o-phosphoric acid (85%) and 40 ml toluene were reacted in an apparatus of the type described in Example 1. After 23.8 g water had been separated off up to a maximum temperature of 200° C., the toluene was removed and 307 g of a colorless liquid having the following composition were obtained:
- 19.1% monoalkyl ester
- 52.3% dialkyl ester
- 16.5% trialkyl ester
- 0.6% o-phosphoric acid
- 7.8% free alcohol
- 3.7% dimethyl cocosamine

EXAMPLE 10

396 g (3.0 moles) n-octanol, 47.4 g (0.2 mole) dimethyl cocosamine, 115.2 g (1.0 mole) o-phosphoric acid (85%) and 50 ml toluene were esterified in the apparatus described in Example 1. The maximum temperature was 201° C. and the quantity of water separated off was 59.1 g. The residue obtained after removal of the toluene contained 38.9% unreacted n-octanol which was separated off substantially quantitatively by distillation under a vacuum of 20 mbar and at a sump temperature of 170° C. The distillate had an iodine number of 0.7. It may be concluded from this that no thermal decomposition of ester to olefins had taken place. The distillation residue of 332g had the following composition:

11.0% monoalkyl ester
57.6% dialkyl ester
17.6% trialkyl ester
0.6% o-phosphoric acid
0.2% n-octanol
13.0% dimethyl cocosamine

COMPARISON EXAMPLE 1

Example 1 was repeated except that no dimethyl cocosamine or other basic inorganic or organic compound in accordance with the invention was added. After a reaction time of 9.5 h, 41.2 g water were separated off for a maximum temperature of 178° C. The reaction temperature ultimately fell to 158° C.

Removal of the toluene left only 197.6 g of residue. The n-octene formed as secondary product during the reaction had also distilled off. The composition of the residue was as follows:

52.7% monoalkyl ester
38.0% dialkyl ester
7.3% trialkyl ester
1.0% o-phosphoric acid
1.0% n-octanol

COMPARISON EXAMPLE 2

Example 8 was repeated except that no dimethyl cocosamine or other basic compound in accordance with the invention was added. Removal of the toluene left a residue of 266.4 g while the quantity of distillate was 94.2 g. The residue had an iodine number of 60 while the distillate had an iodine number of 131. Accordingly, a content of approximately 32% n-dodecane was calculated for the residue.

We claim:
1. A process for the preparation of phosphoric acid alkyl ester mixtures comprising the steps of:
   A. contacting o-phosphoric acid with an alcohol which is one or more of the following:
      (i) a $C_6$–$C_{18}$ fatty alcohol
      (ii) an adduct of a $C_6$–$C_{18}$ fatty alcohol with from 1 to 20 moles of one or both of ethylene oxide and propylene oxide,
      (iii) an adduct of an alkyl phenol having from 8 to 15 carbon atoms in the alkyl group or groups with from 1 to 20 moles of one or both of ethylene oxide and propylene oxide,
   in the presence of from about 0.05 to about 0.2 mole equivalent, based on the quantity of phosphorus atoms in the reaction mixture, of at least one basic inorganic or organic compound, and a water-entraining agent in an amount sufficient to entrain the resulting water of reaction, wherein the ratio of o-phosphoric acid to alcohol is from about 1:1 to about 1:5; and
   B. carrying out a direct esterification reaction at a temperature sufficient to remove the water of reaction with the entraining agent to form a mixture of phosphoric acid alkyl esters.
2. The process of claim 1 wherein the fatty alcohol in (A.i) and (ii) is a saturated alcohol.
3. The process of claim 1 wherein the fatty alcohol in (A.i) and (ii) is a mixture of saturated and unsaturated alcohols.
4. The process of claim 1 wherein in step B. the temperature is at least 160° C.
5. The process of claim 1 wherein in (A.i) and (ii) the fatty alcohol is one or more of the following: hexyl alcohol, 2-ethylhexyl alcohol, heptyl alcohol, octyl alcohol, nonyl alcohol, isononyl alcohol, decyl alcohol, isodecyl alcohol, undecyl alcohol, dodecyl alcohol, tridecyl alcohol, isotridecyl alcohol, tetradecyl alcohol, pentadecyl alcohol, hexadecyl alcohol, heptadecyl alcohol, octadecyl alcohol, oleyl alcohol, elaidyl alcohol and isostearyl alcohol.
6. The process of claim 1 wherein in step A. the at least one basic inorganic or organic compound is an amine or an alkali metal hydroxide.
7. The process of claim 6 wherein the at least one basic inorganic or organic compound is an amine without any additional functional groups and having a molecular weight of from 129 to 297, or potassium hydroxide, or sodium hydroxide.
8. The process of claim 1 wherein unreacted fatty alcohol present in the reaction mixture from step B. is removed from the reaction mixture by vacuum distillation.
9. The process of claim 1 wherein the mixture of phosphoric acid alkyl esters is converted into their alkali metal salts, ammonium salts, or alkanolamine salts.
10. The process of claim 1 wherein in step A. the water-entraining agent is toluene or xylene.
11. A process for the preparation of phosphoric acid alkyl ester mixtures comprising the steps of:
    A. contacting o-phosphoric acid with an alcohol which is one or more of the following:
       (i) a $C_6$–$C_{18}$ fatty alcohol,
       (ii) an adduct of a $C_6$–$C_{18}$ fatty alcohol with from 1 to 20 moles of one or both of ethylene oxide and propylene oxide,
       (iii) an adduct of an alkyl phenol having from 8 to 15 carbon atoms in the alkyl group or groups with from 1 to 20 moles of one or both of ethylene oxide and propylene oxide, wherein in (i) and (ii) the fatty alcohol is one or more of the following: hexyl alcohol, 2-ethylhexyl alcohol, heptyl alcohol, octyl alcohol, nonyl alcohol, isononyl alcohol, decyl alcohol, isodecyl alcohol, undecyl alcohol, dodecyl alcohol, tridecyl alcohol, isotridecyl alcohol, tetradecyl alcohol, pentadecyl alcohol, hexadecyl alcohol, heptadecyl alcohol, octadecyl alcohol, oleyl alcohol, elaidyl alcohol, and isostearyl alcohol, in the presence of from about 0.05 to about 0.2 mole equivalent, based on the quantity of phosphorus atoms in the reaction mixture, of at least one of an amine without any additional functional groups and having a molecular weight of from 129 to 297, potassium hydroxide, and sodium hydroxide, and a water-entraining agent which is toluene and/or xylene in an amount sufficient to entrain resulting water of reaction, wherein the ratio of o-phosphoric acid to alcohol is from about 1 to about 1:5;
    B. carrying out a direct esterification reaction at a temperature of at least 160° C. to remove the water of reaction with the entraining agent to form a mixture of phosphoric acid alkyl esters; and
    C. removing unreacted fatty alcohol present in the reaction mixture from step B. from the reaction mixture by vacuum distillation.
12. The process of claim 11 wherein the mixture of phosphoric acid alkyl esters is converted into their alkali metal salts, ammonium salts, or alkanolamine salts.

* * * * *